(12) United States Patent
Myers et al.

(10) Patent No.: US 6,929,705 B2
(45) Date of Patent: Aug. 16, 2005

(54) ANTIMICROBIAL COATED METAL SHEET

(75) Inventors: Frederick A. Myers, Middletown, OH (US); LeRoy R. Price, West Chester, OH (US)

(73) Assignee: AK Steel Corporation, Middletown, OH (US)

( * ) Notice: Subject to any disclaimer, the term of this patent is extended or adjusted under 35 U.S.C. 154(b) by 79 days.

(21) Appl. No.: 09/938,205

(22) Filed: Aug. 23, 2001

(65) Prior Publication Data

US 2002/0185199 A1 Dec. 12, 2002

Related U.S. Application Data (60) Provisional application No. 60/287,615, filed on Apr. 30, 2001.

(51) Int. Cl.[7] .................................................. C23C 22/00
(52) U.S. Cl. .................... 148/243; 148/251; 148/259; 148/262; 427/332; 427/341; 427/656; 428/668; 428/564; 428/457; 428/472.3; 106/813; 516/87
(58) Field of Search .......................... 148/243, 240, 148/251, 259, 262; 427/332, 341, 656; 428/668, 564, 457, 472.3; 106/813; 516/87

(56) References Cited

U.S. PATENT DOCUMENTS

| | | | |
|---|---|---|---|
| 2,550,489 A | | 3/1951 | Martin et al. |
| 3,930,899 A | * | 1/1976 | Sakamaki et al. .......... 428/651 |
| 3,983,053 A | | 9/1976 | Courtney et al. |
| 4,000,100 A | | 12/1976 | Baldyga |
| 4,250,081 A | | 2/1981 | Bode et al. |
| 4,486,488 A | | 12/1984 | Pietsch et al. |
| 4,525,410 A | | 6/1985 | Hagiwara et al. |
| 4,742,164 A | | 5/1988 | Iguchi et al. |
| 4,766,229 A | | 8/1988 | Kobayashi et al. |
| 4,775,585 A | | 10/1988 | Hagiwara et al. |
| 4,801,445 A | | 1/1989 | Fukui et al. |
| 4,906,464 A | | 3/1990 | Yamamoto et al. |
| 4,911,898 A | | 3/1990 | Hagiwara et al. |
| 4,911,899 A | | 3/1990 | Hagiwara et al. |

(Continued)

FOREIGN PATENT DOCUMENTS

| | | |
|---|---|---|
| DE | 19535650 | 6/1996 |
| EP | 1 018 546 A1 | 7/2000 |
| JP | 52-092000 | 7/1977 |
| JP | 55-38358 | 3/1980 |
| JP | 55-164236 | 12/1980 |

(Continued)

OTHER PUBLICATIONS

Business Description, HealthShield Technologies L.L.C., May 1, 2000, 47 pgs.

(Continued)

*Primary Examiner*—Roy King
(74) *Attorney, Agent, or Firm*—Frost Brown Todd LLC (57) ABSTRACT

The present invention relates to metallic sheets having an improved antimicrobial property and also related to a method of manufacturing such sheets. More particularly, it relates to the continuous coating on metallic sheets with a resin composition containing antimicrobial additives. The surface of the metallic article is afforded antimicrobial properties by coating a liquid dispersion or solution of fine particles made of an antimicrobial ingredient on the surface of the metallic sheet dispersed in a uniform layer and cured or dried to affix to the metallic surface. The inorganic antibacterial particles are metal component-supporting oxides and zeolite powders. The inorganic antibacterial core particles have at least a primary surface coating of at least one metal or metal compound having antimicrobial properties. Roll coaters apply the coating. The metallic article generally includes sheet articles made of metals, for example, metallic sheets made of stainless steel, conventional steel sheets and aluminum sheets or plate.

12 Claims, 3 Drawing Sheets

U.S. PATENT DOCUMENTS

| | | | |
|---|---|---|---|
| 4,938,955 A | 7/1990 | Niira et al. | |
| 4,938,958 A | 7/1990 | Niira et al. | |
| 5,003,638 A | 4/1991 | Miyake et al. | |
| 5,047,448 A | 9/1991 | Tanaka et al. | |
| 5,085,416 A | 2/1992 | Miyake et al. | |
| 5,094,847 A | 3/1992 | Yazaki et al. | |
| 5,100,671 A | 3/1992 | Maeda et al. | |
| 5,112,486 A | 5/1992 | Fujiwara et al. | |
| 5,116,575 A | 5/1992 | Badertscher et al. | |
| 5,180,402 A | 1/1993 | Kubota et al. | |
| 5,180,585 A | 1/1993 | Jacobson et al. | |
| 5,208,016 A | 5/1993 | Ohmae et al. | |
| 5,238,749 A | 8/1993 | Cueman et al. | |
| 5,264,250 A | 11/1993 | Steele et al. | |
| 5,305,827 A | 4/1994 | Steele et al. | |
| 5,387,473 A | 2/1995 | Yoshimi et al. | |
| 5,433,424 A | 7/1995 | Watanabe | |
| 5,436,282 A | 7/1995 | Gustafsson et al. | |
| 5,556,699 A | 9/1996 | Niira et al. | |
| 5,634,986 A * | 6/1997 | Beck | 148/246 |
| 5,670,261 A | 9/1997 | Kameya et al. | |
| 5,681,575 A | 10/1997 | Burrell et al. | |
| 5,681,890 A | 10/1997 | Tanaka et al. | |
| 5,723,110 A | 3/1998 | Yamamoto et al. | |
| 5,837,275 A | 11/1998 | Burrell et al. | |
| 5,861,068 A | 1/1999 | Hasegawa et al. | |
| 5,954,892 A * | 9/1999 | Musingo et al. | 106/14.12 |
| 5,985,308 A | 11/1999 | Burrell et al. | |
| 6,017,553 A | 1/2000 | Burrell et al. | |
| 6,093,407 A | 7/2000 | Cummings et al. | |
| 6,180,162 B1 | 1/2001 | Shigeru et al. | |
| 6,306,341 B1 | 10/2001 | Yokota et al. | |

FOREIGN PATENT DOCUMENTS

| | | | |
|---|---|---|---|
| JP | 57-77022 | 5/1982 | |
| JP | 59-133235 | 7/1984 | |
| JP | 60-64611 | 4/1985 | |
| JP | 60-79433 | 5/1985 | |
| JP | 59-37956 | 6/1985 | |
| JP | 60-100504 | 6/1985 | |
| JP | 60-174707 | 9/1985 | |
| JP | 60-178810 | 9/1985 | |
| JP | 60-181002 | 9/1985 | |
| JP | 60-181370 | 9/1985 | |
| JP | 60-184325 | 9/1985 | |
| JP | 60-202162 | 10/1985 | |
| JP | 61-137564 | 6/1986 | |
| JP | 61-138647 | 6/1986 | |
| JP | 61-138658 | 6/1986 | |
| JP | 61-138795 | 6/1986 | |
| JP | 60-136796 | 12/1986 | |
| JP | 62-7746 | 1/1987 | |
| JP | 62-7747 | 1/1987 | |
| JP | 62-7748 | 1/1987 | |
| JP | 62-41775 | 2/1987 | |
| JP | 62-70221 | 3/1987 | |
| JP | 60-136795 | 6/1987 | |
| JP | 62-195037 | 8/1987 | |
| JP | 62-195038 | 10/1987 | |
| JP | 62-238900 | 10/1987 | |
| JP | 62-241932 | 10/1987 | |
| JP | 62-241939 | 10/1987 | |
| JP | 62-243665 | 10/1987 | |
| JP | 61-103401 | 11/1987 | |
| JP | 61-232253 | 4/1988 | |
| JP | 01254782 | 10/1989 | |
| JP | 03188168 A * | 8/1991 | |
| JP | 08325482 | 1/1993 | |
| JP | 08325482 A * | 12/1996 | C09D/05/14 |

OTHER PUBLICATIONS

Brochure, AK Steel Products Coated With the AgION™ Antimicrobial Compound, Nov., 2000, 6 pgs.

Brochure, Antimicrobial ZEOMIC™, "Inorganic Antimicrobial to Satisfy Diverse Needs", Sinanen Co., Ltd., 12 pgs. (no date).

Brochure (tri–fold), HealthShield Technologies,"The Most Advanced Antimicrobial Silver Delivery System." (no date).

Letter from US EPA to AgION Tech LLC dated Feb. 16, 2001.

Letter from NSF International to AK Steel Corporation dated Aug. 31, 2000.

"AK aids with first anti–germ home," Middletown Journal, Mar. 6, 2001.

"Cleaner Than Thou," The New York Times Magazine, May 27, 2001.

Leach, R.C., "The Preparation, Powder Coating, and Curing of Precut Metal Sheets for Postforming," Metal Finishing, Elsevier Science Publishing, New York, NY, US, vol. 93, No. 4, Apr. 1, 1995, pp. 24, 26–27.

* cited by examiner

ANTIMICROBIAL COATED METAL SHEET

CROSS REFERENCE TO RELATED APPLICATIONS

This application claims priority under 35 U.S.C. 119 to U.S. provisional application Ser. No. 60/287,615, filed Apr. 30, 2001 and entitled "Antimicrobial Coated Metal Sheet" the disclosure of which is hereby expressly incorporated herein by reference.

FIELD OF THE INVENTION

The present invention relates to metallic sheets having an improved antimicrobial property and also related to a method of manufacturing such sheets. More particularly, it relates to the continuous coating on metallic sheets with a resin composition containing antimicrobial additives.

BACKGROUND OF THE INVENTION

Recently there has been a trend to develop materials possessing an antimicrobial property generally utilizing a metal, e.g., silver, copper, zinc, etc. Metallic articles, especially stainless steel sheets, are known for their hygienic cleanliness. For example, with stainless steel, it is known to add antibacterial properties using metallic layers or alloy layers of chromium, titanium, nickel or iron containing silver, copper and/or zinc formed on their surface by sputtering or incorporating silver in the stainless steel and dispersing silver phases. In addition, it has been known for a long time that silver ions or copper ions or zinc ions have an antibacterial property. For example, a silver ion has widely been used as a disinfectant in the form of silver nitrate. However, the use of silver nitrate as a solution is inconvenient for handling and would have limited durability.

Generally, the incorporation of silver into a metal object or article itself has the disadvantage that the metal's characteristics are altered by the inclusion of the silver as well as the disadvantage of the high cost of the metals themselves. Such a metallic sheet or plate having the antibacterial ingredient deeply imbedded inside the sheet or plate does not exert any effective action upon bacteria attached to the surface making incorporation throughout the entire article uneconomical.

Known thermoset resin compositions have been broadly used as coating materials for various metals such as iron, aluminum, copper, and stainless steel since the compositions afford a coating which is superior in luster, transparency, hardness, weather resistance, chemical resistance and other properties. However, the coating, itself would have no antibacterial action in and of itself and such coatings often have insufficient adhesion to metals making it impossible to endure a forming process such as bending. As is apparent from the foregoing, an object of the present invention is to provide an antibacterial resin composition for coating of metals which withstands bending or forming processes and is usable for coated metal sheets.

SUMMARY OF THE INVENTION

The present invention provides a polymer composition containing oxide or zeolite particles and having an antibacterial property along with processes for coating the surface of metal sheets with such composition. Specifically, the present invention provides for a metal sheet coated with a polymer resin containing inorganic particles with antibacterial properties and the process for making such coated sheets.

The inorganic antibacterial particles are metal component-supporting oxides and zeolite powders that are made from core particles selected form the group consisting of oxides of titanium, aluminum, zinc and copper, sulfates of calcium, strontium and barium, zinc sulfide, copper sulfide, zeolites, mica, talc, kaolin, mullite, zirconium phosphate and silica.

Preferably, the particles are at least one zeolite at least part of which retains at least one metal ion having a bactericidal property at the ionic exchange sites of the zeolite particles.

The inorganic antibacterial core particles have at least a primary surface coating or constituent, comprising of from about 0.05 to about 20% by weight based on the core particles, of at least one metal or metal compound having antimicrobial properties selected from the group consisting of silver, copper, zinc, mercury, tin, lead, bismuth, cadmium, chromium, cobalt, nickel, and thallium ions or mixtures thereof. Preferably, the coating or constituent is at least one metal or metal compound having antimicrobial properties selected from the group consisting of silver, copper, zinc, and mixtures thereof.

According to one embodiment of the present invention, there is provided a metallic sheet having an antibacterial property characterized in that the sheet is coated with a polymer composed of at least one polymer in which is dispersed at least one zeolite at least part of which retains at least one metal ion having a bactericidal property at the ionic exchange sites of the zeolite particles and methods for producing such metal sheets.

The process according to the present invention is characterized by admixing zeolite particles retaining at least one metal ion having a bactericidal property with a polymer or a mixture of polymers prior to coating onto a metallic sheet. Preferably, the zeolite particles retain the metal ions having bactericidal properties at ionic exchange sites of the zeolite in an amount less than the ion exchange saturation capacity of the zeolite.

The method of the present invention comprises the steps of (a) cleaning the surface by chemical or mechanical means; (b) surface preparation or pretreatment of the metal surface by coating with a pretreatment layer appropriate to the base metal to gain proper adhesion properties; (c) coating the surface of the pretreated metal sheet with a uniform layer of an oxide, zeolite or phosphate containing resin and (d) subjecting the coated metal article to curing conditions to cure or dry the resin to produce a hardened and adhered coating to the final sheet product.

After curing, the applied coating composition, a metal sheet having a cured resin coating adhered thereto is formed generally having antimicrobial properties. Also, the coating that is formed, typically, has improved fingerprint resistance.

The film coatings can be used to control the growth of harmful bacteria, mold and mildew. These film coatings may be applied to stainless or carbon steel products for use in a variety of applications. On stainless steels, the zeolite refractory compound, when added to a clear resin coating, masks the appearance of fingerprints and smudges due to the light scattering influence of the zeolite particles contained within the coating matrix. The coating also protects the surface from staining when tested against kitchen spills such as ketchup, mustard and pickle juice.

Generally, a silver-bearing refractory compound is incorporated into polyester or epoxy film coatings to control the growth of harmful bacteria, mold and mildew. These film coatings may be economically applied to stainless or carbon steel products on full size production coils by means of roll coating. The antimicrobial properties may last for years depending on the intended application. Clear or pigmented film coatings can be used.

Preferably, silver ions are encapsulated within a zeolite refractory. The zeolite powder is blended into either a polyester or epoxy resin. A thin film coating, about 0.00025" thick, is applied to either a carbon or stainless steel sheet. The silver ions have great mobility and can diffuse to the surface of the steel to inhibit the growth of bacteria and mold.

Silver has long been recognized for its safe antimicrobial properties. Coated products may be effective against many common food borne pathogens such as *Escherichia coli*, *Salmonella* and *Listeria monocytogenes* as well as various types of mold including *Aspergillus niger*.

DETAILED DESCRIPTION OF THE INVENTION

The present invention provides precoated metal sheets such as iron and steel sheets, aluminum sheets, galvanized and aluminized steel sheets, and stainless steel sheets coated with a polymer containing inorganic antibacterial particles before the metal sheets are mechanically worked into complex shapes as by die pressing, bending, embossing, rolling, and drawing. The inorganic antibacterial particles are metal component-supporting oxides and zeolite powders that are made from core particles selected form the group consisting of oxides of titanium, aluminum, zinc and copper, sulfates of calcium, strontium and barium, zinc sulfide, copper sulfide, zeolites, mica, talc, kaolin, mullite, zirconium phosphate and silica.

For convenience herein, the expression "antimicrobial" or "antibiotic" is used generally to include antibacterial, antifungal, antialgal, antiviral, antiprotozoan and other such activity. The antimicrobial film of the present invention is particularly effective to the following bacteria, fungi and yeast: *Bacillus cereus* var *mycoides*, *Escherchia coli*, *Pseudomonas aeruginosa*, *Staphylococcus aureus*, *Streptococcus feacalis*, *Salmonella gallinarum*, *Vibrio parahaemdyticus*, *Candida albicans*, *Streptococcus mutans*, *Legionella pneumophila*, *Fuso bacterium*, *Aspergillus niger*, *Aureobasidium pullulans*, *Cheatomium globosum*, *Gliocladium virens*, *Pencillum funiculosum* and *Saccharomyces cerevisiae*.

Figure 2:
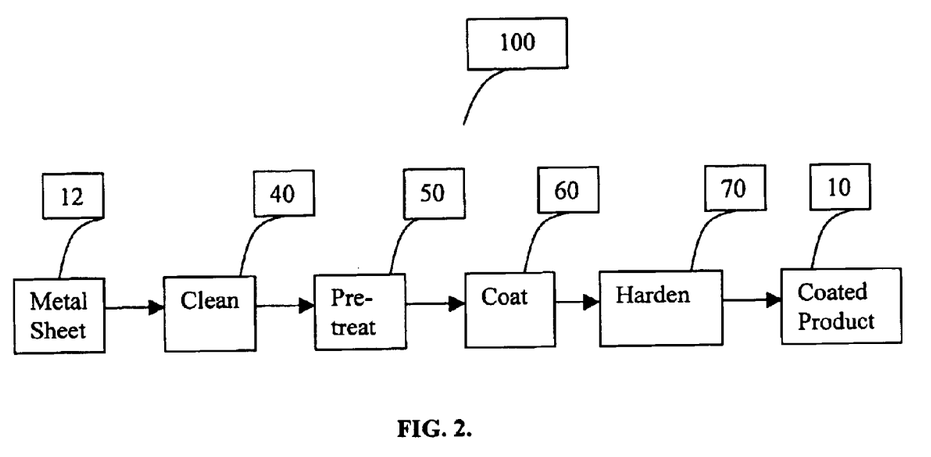
FIG. 2 shows flow chart of the process for producing metal sheets coated with a polymer containing an antimicrobial oxide or zeolite.

The method of the present invention comprises the steps of (a) cleaning the surface by chemical or mechanical means 40; (b) surface preparation or pretreatment 50 of the metal surface by coating with a pretreatment layer appropriate to the base metal to gain proper adhesion properties; (c) coating 60 the surface of the pretreated metal sheet with a uniform layer of a resin containing a metal component-supporting oxide, phosphate or zeolite powder and (d) subjecting the coated metal article to conditions 70 to cure or dry the resin to produce a hardened and adhered coating to the final sheet product.

The inorganic antibacterial core particles has at least a primary surface coating or constituent, comprising of from about 0.05 to about 20% by weight based on the core particles, of at least one metal or metal compound having antimicrobial properties selected from the group consisting of silver, copper, zinc, mercury, tin, lead, bismuth, cadmium, chromium, cobalt, nickel, and thallium ions or mixtures thereof. Preferably, the coating is at least one metal or metal compound having antimicrobial properties selected from the group consisting of silver, copper, zinc, and mixtures thereof.

Figure 1:
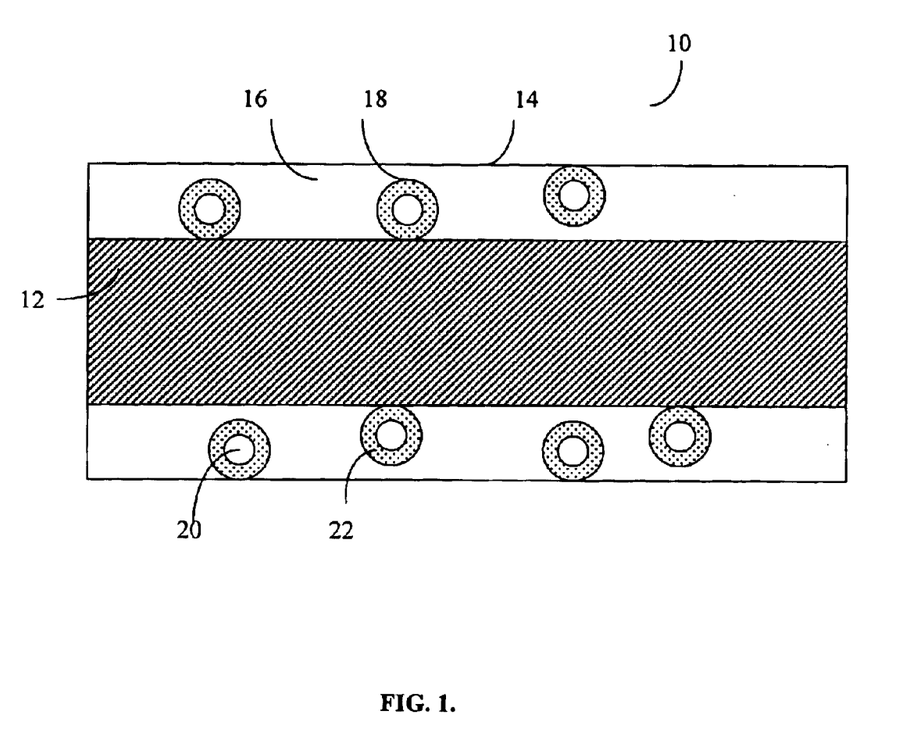
FIG. 1 is a diagrammatic sectional view of a sheet metal according to the present invention.

A coated sheet metal according to the invention, indicated by the general reference 10, can be seen in FIG. 1. As used herein, the term "sheet" or "strip" refers to a length of flat metal material of any width formed in continuous strips or cut to specific lengths. Generally, the sheet is a flat rolled metal product with a width to thickness ratio greater than about 25 and a thickness of less than about 0.250 inches.

Sheet 10 comprises a substrate consisting of a metal sheet 12 made from metal or metal alloys selected from the group consisting of aluminum, iron, nickel, titanium, molybdenum, magnesium, manganese, copper, silver, lead, tin, chromium, beryllium, tungsten and cobalt, and alloys of two or more thereof. Examples of the alloys are alloy steels such as carbon steel, nickel steel, chromium steel, nickel-chromium steel, chromium-molybdenum steel, stainless steel, silicon steel and Permalloy; aluminum alloys such as Al—Cl, Al—Mg, Al—Si, Al—Cu—Ni—Mg and Al—Si—Cu—Ni—Mg; copper alloys such as brass, bronze, silicon bronze, silicon brass, nickel silver and nickel bronze; nickel alloys such as nickel manganese (D nickel), nickel-aluminum (Z nickel), and nickel-silicon.

Further as the aluminum-based metal, there can be used pure aluminum; aluminum oxide; and aluminum alloys for casting and expanding such as Al—Cu, Al—Si, Al—Mg, Al—Cu—Ni—Mg, Al—Si—Cu—Ni—Mg alloys, high tensile aluminum alloy and corrosion resistant aluminum alloy. Also as the iron-based metals, there can be used pure iron, iron oxide, carbon steel, nickel steel, chromium steel, nickel-chromium steel, chromium-molybdenum steel, nickel-chromium-molybdenum steel, stainless steel, silicon steel, Permalloy, non-magnetic steel, magnet steel, cast steel, etc. Preferably, the metal sheet is selected from the group consisting of stainless steel, carbon steel, iron, aluminum, aluminized steel, galvanized steel, aluminum and steel alloys, magnesium, and magnesium alloys.

On one or both of its faces, sheet 12 is coated with an antimicrobial film layer 14 comprising an organic polymer 16. The polymer 16 has inorganic antimicrobial powders 18 dispersed within the polymer comprising an oxide or zeolite core 20 with at least a primary surface coating or constituent of an antimicrobial metal 22.

The steels that may be employed for the manufacture of the metal sheet 12 are of various types. One type corresponds to ferritic grade stainless steels that contain 17 wt. % of chromium (Cr) with or without molybdenum (Mo) referred to according to the US Standard as AISI409, AISI 430, AISI 434, AISI 439 and AISI 444, and the French Standard as Z3CTNb18. A second type corresponds to austenitic grades that contain from about 16 to about 18 wt. % of chromium and at least 2 wt. % of nickel (Ni) with or without molybdenum, referred to according to the US Standard as AISI 304 and AISI 316. Other stainless steels can be employed, provided that they contain at least 11 wt. % of chromium. It is possible, for example, to employ a ferritic steel sheet 12 containing, on a mass basis, from about 11 to about 20 wt. % of chromium and from about 0.2 to about 2 wt. % of nickel.

In coil-coating processes, a continuous strip of sheet metal is uncoiled at the line entrance and recoiled at the exit, having been coated or otherwise treated. The line speeds can be up to 200 m/min.

A process that will be described below manufactures the coated sheet metal 10.

1. Surface Cleaning

A degreasing operation is recommended to guarantee a good adherence of the coating. In fact, if the surface of the metal sheet is not degreased, the fatty substances and other surface contaminants that are not removed are liable to reduce the adherence of the resin coating and to give rise to a nonhomogeneous deposit comprising areas without coating.

The metal substrate is desirably free of contaminants, such as petroleum greases and oils, that may cause the pretreatment and coating to be insufficiently adhered to the metal substrate. Consequently, it is desirable, prior to applying the coating composition, to clean the metal substrate. Various methods of cleaning are well known in the art. The particular cleaning method should be able to adequately remove residual oil or dirt from the surface but should not cause over-etching of the metal surface. Exemplary cleaning methods include solvent cleaning (such as a chlorinated solvent (e.g., methylene chloride), ketone (e.g., acetone), alcohol (e.g., methanol), or toluene, emulsion cleaning, alkaline cleaning, acid cleaning, pickling, salt bath descaling ultrasonic cleaning, roughening (e.g., abrasive blasting, barrel finishing, polishing and buffing, chemical etching and electro-etching).

The degreasing of the sheet metal is generally performed either chemically or electrolytically. The surface of the work piece of metal may alternatively be cleaned by mechanical means (grinding or sandblasting). The main object of the grinding or sandblasting procedure is to remove impurities or oxides on the surface, to prevent impurities from contaminating the surface alloy layer. In the mean time, the surface roughness will be increased after this procedure, which facilitates the adhesion of coating. Silicon carbonate sandpaper of #180 to #600 is suitable for grinding. Silica sand or other mineral sand can be used in sandblasting. The sheet metal can be degreased chemically by being placed in contact with a solution containing halogenated organic solvents such as methylene chloride, 1,1,1-trichloroethane, perchloroethylene or trichloroethylene.

The degreasing operation may be performed electrolytically in an electrolysis bath or electrolyte consisting of an aqueous solution containing alkaline mixtures similar to those just specified or else calcium carbonate or potassium hydroxide. The electrolyte may contain an alkaline compound in a proportion of from about 0.5 to about 20 wt. %. The temperature of the electrolyte may be between from about 25° and about 95° C. The sheet metal may be subjected to a current density of between 0.1 and 20 A/dm$^2$ for a period longer than about 0.1 seconds.

The sheet metal can also be degreased chemically by employing a solution based on alkaline mixtures containing one or more agents selected from the group consisting of caustic soda, soda ash, alkaline silicates, sodium hydroxide, sodium carbonate, sodium metasilicate, phosphates, alkaline builders, ammonium acid phosphate, ammonium hydroxide, monoethanol amine, and dimethylamine oxide and optionally containing one or more of the agents selected from the group consisting of complexing agents, surfactants, sequestrant, builders, surface-active agents, defoaming agents, and mixtures thereof. The alkaline degreasing solutions and alkaline degreasing agents employed for cleaning metal surfaces are well known in the literature. Exemplary methods will use a solution of potassium or sodium hydroxide at a concentration of from about 1 to about 5%. The degreasing solution is applied to the surface of the metal sheet by known spray or dip methods. Generally, these are applied at a temperature of from about 50 to about 200° C., preferably from about 60 to about 80° C.

Alkaline builders may be generally classified into three types, namely, the strong alkaline type composed mainly of sodium silicate or trisodium phosphate and/or caustic soda, medium alkaline type composed of one or more than one of the following; disodium phosphate, sodium pyrophosphate, sodium carbonate, etc., and mild alkaline type composed of disodium phosphate, sodium bicarbonate, sodium tripolyphosphate, sodium sesquicarbonate, etc. Any alkaline builder of the above types may be employed therefor.

The temperature of the alkaline solution is generally between about 25° and about 95° C. Preferably, the temperature of the alkaline solution is greater than about 50° C. More preferably, the temperature is greater than about 60° C. The sheet metal is generally subjected to the solution for a period longer than 0.1 second. Preferably, the sheet metal is subjected to the alkaline solution for a period longer than 1 second. More preferably, the sheet metal is subjected to the alkaline solution for a period longer than 3 seconds.

The cleaning bath may have any appropriate pH suitable for the process conditions and compatible with the equipment. For example, if the equipment is mild steel that is prone to corrosion under acidic conditions, the pH of the cleaning bath should not be so low as to cause acid corrosion. The cleaning bath may be mildly acidic if ammonium acid phosphate is selected as the cleaning agent and, more specifically, has a pH of from about 2.0 to about 7.5, preferably the agent has a pH of from about 2.0 to about 5.5, more preferably the agent has a pH of from about 2.0 to about 3.5. Alternatively, the cleaning bath may be mildly alkaline if ammonium hydroxide is selected as the cleaning agent and, more specifically, has a pH of from about 7.0 to about 12, preferably the agent has a pH of from about 7.0 to about 11, more preferably the agent has a pH of from about 8.0 to about 10.0.

The concentration of the cleaning agent and the surfactant must be sufficient to remove substantially all oil and other contaminants from the metal surface, but must not be so high that a significant amount of foaming occurs. Typically, the water rinse step may be avoided if the cleaning bath is not too concentrated, which is acceptable in the event that the metal is initially relatively clean.

The metal surface having been contacted by the cleaning solution is generally rinsed with water (neutral medium) or other known rinse agent, also by known spray or dip methods. Air-drying or other drying means generally follows rinsing.

The surface cleaning step may be eliminated or combined with the surface pre-treatment step in certain circumstances depending upon the condition of the metal and the type of pre-treatment utilized.

2. Surface Pre-Treatment

The metal sheet is preferably pretreated to enhance the adhesion of the coating composition after curing. The pretreatment may be, for example, the formation of an interlayer on the metal substrate surface that enhances adhesion of the coating composition after curing. For example, the interlayer may be a chemical conversion layer (i.e., coating), such as a silane, phosphate, chromate, epoxy, or oxide coating or the interlayer may be an adhesive coating. Generally, the pretreatment is by contacting the metal with chromium phosphate, chromium chromate, zinc phosphate, iron phosphate, or an organic epoxy-based composition.

The interlayer may be any thickness sufficient to enhance the adhesion of the coating composition during application and after curing but, in general, the interlayer is at most about 100 percent of the thickness of the cured coating of the antimicrobial composition on one side, preferably the interlayer is at most about 50 percent of the thickness of the cured coating of the antimicrobial composition, and more preferably the interlayer is at most about 10 percent of the thickness of the cured coating of the antimicrobial composition. The interlayer, typically, is between about 0.01 to about 30 microns thick. Preferably thickness of the interlayer is at least about 0.1 microns, more preferably at least about 0.2 microns and most preferably at least about 0.5 microns. Preferably the thickness of the interlayer is at most about 20 microns, more preferably at most about 15 microns and most preferably at most about 10 microns.

Generally, the metal surface is pretreated with an aqueous composition comprising phosphoric acid and a divalent metal ion when the metal substrate is steel, zinc or zinc based alloys or zinc aluminum alloy coated steel, aluminum or aluminum alloy. Any divalent metal ion may be used as the divalent metal ion for use in the composition. Generally, the metal is selected from the group consisting of divalent transition metal ions, such as Mn, Co, Fe, Ni, and Zn, and alkaline earth divalent metal ions, such as Mg, Ca, Sr, and Ba. Preferably the divalent metal ion is other than nickel for environmental reasons. Preferably the metal is selected from the group consisting of Fe and Zn. Most preferably, the metal is Zn. Silicate may be added to precipitate out any titanium ions that can then be removed from the phosphating composition.

To accelerate the formation of the phosphate layer, oxidants such as bromate, chlorate, nitrate, nitrite, organic nitro compounds, perborate, persulfate or hydrogen peroxide, m-nitrobenzene sulfonate, nitrophenol or combinations thereof.

To optimize the layer formation on certain materials, there is for instance added sulfate, simple or complex fluoride ions, silicofluoride, boron fluoride, citrate, tartrate, hydroxycarboxylic acids, aminocarboxylic acids, condensed phosphates, or SiO-containing compounds (e.g., alkali metal metasilicate, alkali metal orthosilicate, and alkali metal disilicate) and mixtures thereof may be added.

When the metal surface is predominantly galvanized metal and/or steel, the pretreatment comprises contacting the metal surface with an aqueous composition comprising phosphoric acid and a divalent metal ion, the composition generally having a total phosphate content from about 0.01 to about 3 moles/liter, preferably a total phosphate content from about 0.02 to about 2 moles/liter, and more preferably a total phosphate content from about 0.1 to about 1 moles/liter. The composition also generally having divalent metal ion content of from about 0.001 to about 2 moles/liter (based on metal ion content), preferably a metal ion content of from about 0.01 to about 1 moles/liter, and more preferably a metal ion content of from about 0.05 to about 0.5 moles/liter.

In case of an aluminum, aluminum alloy, or aluminized steel sheet, in order to enhance corrosion resistance, surface hardness and adhesive property of the substrate, it is preferable to form an oxide film (alumite) on the sheet by pretreatment (anodizing) with caustic soda, oxalic acid, sulfuric acid or chromic acid.

The quantities of the components in the composition can vary but are preferably chosen to suit the particular metal which is prevalent in the surface being treated and therefore depends upon whether the metal surface being treated is mainly steel, galvanized, aluminum or a aluminum/zinc alloy.

In particular, for use on aluminum surfaces, it is preferable that the aqueous composition should also include an activator preferably fluoride ions. Generally fluoride ions will be provided in the form of hydrogen fluoride. Fluoride is generally present in amounts up to 1.0 moles/liter, preferably in amounts up to 0.5 moles/liter, and more preferably in amounts up to 0.25 moles/liter.

In particular in the compositions for pretreatment of galvanized metals or steel metal surfaces, preferably the composition also includes boric acid. When the prevalent metal surface for coating is galvanized, boric acid is generally present in an amount of at least 0.02 moles/liter, preferably in an amount of at least 0.05 moles/liter, and more preferably in an amount of at least 0.1 moles/liter.

In particular in the compositions for pretreatment of stainless steel metals or stainless steel metal surfaces, preferably the surface pretreatment is an epoxy or other organic based pretreatment.

The pretreatment compositions can be prepared by the addition of the components in any convenient order. The phosphating is generally aimed at providing a fast and efficient treatment for a coil coating metal conversion process.

For coil coating, the pretreatment coating is generally applied by roll coating or reverse roll coating, or by passing the metal sheet through a spray or bath of the composition. However, any other standard application form can be used such as by spraying or conventional spray/dip treatment. Preferably, phosphate pretreatments will be by dip treatment and epoxy pretreatments will be by roll coating. The applied pretreatment should cover any desired area of the metal substrate to be coated by the final antimicrobial polymer.

The sheet metal is generally subjected to the solution for a period longer than 0.1 second. Preferably, the sheet metal is subjected to the alkaline solution for a period longer than 1 second. More preferably, the sheet metal is subjected to the pretreatment solution for a period longer than 10 seconds.

The pretreatment of the metallic sheet is generally followed by a rinsing with water or other neutral rinse medium or dilute chromic acid by known spray or dip methods to remove residual pretreatment solution. This stage is optionally used to ensure removal of any pretreatment residues or to seal or cure the pretreatment surface with a final rinse agent. Air-drying or other drying means generally follows rinsing.

The pretreatment is generally dried by heating and this may be carried out by conventional means, for example by passing the coil or coated article through an oven or exposing to IR radiation. The drying temperature is generally between about 25° and about 95° C. Preferably the temperature reached on drying or curing is at least 50° C. More preferably the temperature reached on drying or curing is at least 60° C. Once the coated metal surface has been dried, the antimicrobial coating can be immediately applied.

3. Coating Composition

The antimicrobial coatings of the present invention are organic polymer compositions containing antimicrobial metal-supporting oxide or zeolite particles.

To prepare the coating composition, any sequence of mixing the constituents sufficient to form the coating composition may be employed. The mixing or emulsification technique employed may be any suitable technique, such as those known in the art. Exemplary mixing techniques include ball, bead or sand milling, high shear mixing, sonic mixing, attritor milling and rapid shaking.

a. Inorganic Antibacterial Particles

The inorganic antibacterial particles are metal component-supporting oxides and zeolite powders that are core particles selected form the group consisting of oxides of titanium, aluminum, zinc and copper, sulfates of calcium, strontium and barium, zinc sulfide, copper sulfide, zeolites, mica, talc, kaolin, mullite, silica, zirconium and zirconium phosphate.

The inorganic antibacterial core particles have at least a primary surface coating or constituents, comprising of from about 0.05 to about 20% by weight based on the core particles, of at least one metal or metal compound having antimicrobial properties selected from the group consisting of silver, copper, zinc, mercury, tin, lead, bismuth, cadmium, chromium, cobalt, nickel, and thallium ions or mixtures thereof. Preferably, the coating is at least one metal or metal compound having antimicrobial properties selected from the group consisting of silver, copper, zinc, or mixtures thereof and mixtures thereof. Preferably, the amount of antimicrobial component on or in the core particle is at least about 0.1% by weight, more preferably at least about 0.2% by weight, and most preferably at least about 0.5% by weight. Preferably, the amount of antimicrobial component on or in the core particle is at most about 20% by weight, more preferably at most about 15% by weight, and most preferably at most about 10% by weight.

The inorganic antibacterial metal component-supporting oxides and zeolite may additionally be coated with a secondary, protective layer selected from the group consisting of silica, silicates, silicon dioxide, borosilicates, aluminosilicates, alumina, aluminum phosphate, zinc, zinc oxide, zinc silicate, copper, copper oxide, silanes, and mixtures thereof, among others. The secondary protective layer normally comprises from about 0.1 to about 20% by weight. Preferably, the amount of secondary protective coating layer on the metal-containing particle is at least about 0.5% by weight, more preferably at least about 0.2% by weight, and most preferably at least about 1.0% by weight of the coated particle composition. Preferably, the amount of secondary protective coating layer on the metal-containing particle is at most about 10% by weight, more preferably at most about 5% by weight, and most preferably at most about 3% by weight of the coated particle composition.

It will be appreciated by those skilled in the art that if relatively fine core particles are employed when practicing the invention, then the practitioner should ensure substantially total surface coverage of the first coated core material. While the protective layer can be quite dense, the protective layer should be sufficiently porous to permit diffusion of the antimicrobial component through the coating at an effective rate and function as a barrier that limits, if not eliminates, interaction between the antimicrobial component and a surrounding matrix.

The inorganic antibacterial metal component-supporting oxides and zeolites, with or without a secondary, protective layer, may additionally be coated with a dispersion enhancing coating such as a suitable resin or a hydrous metal oxide, e.g., alumina, hydrous alumina, zirconia, mixtures thereof, among others. This coating corresponds to about 0.1% to at least about 5% by weight and normally about 0.5 to about 3% by weight based on the core material.

The amount of a dispersion aid that is present in the antimicrobial composition ranges between about 0.1% and at least about 2.0% by weight based upon the antimicrobial powder, with about 0.5% to about 1% by weight normally being effective.

It will be appreciated by those skilled in the art that the ratio of the secondary coatings and dispersion aids can vary widely and may be readily selected by the artisan.

The process for preparing the inorganic antibacterial metal component-supporting oxide composition of the invention is described in greater detail in U.S. Pat. No. 5,180,585; the disclosure of which is incorporated herein by reference.

Preferably, the inorganic antibiotic particle is an antibiotic zeolite. The "antibiotic zeolites" used in the invention are those of which ion-exchangeable ions are partially or completely ion-exchanged with antibiotic ions. Antibacterial metal-supporting zeolite is known per se and may be prepared by ion-exchanging zeolite with antibacterial metals. Examples of the antibacterial metals include silver, copper, zinc, mercury, tin, lead, bismuth, cadmium, chromium, cobalt, nickel, and thallium ions or mixtures thereof. Preference is given to silver, copper, zinc, or mixtures thereof. Particularly, silver alone or a combination of silver with copper or zinc is excellent in antibacterial properties. Methods for preparing antibacterial zeolite are described in, for example, U.S. Pat. Nos. 4,525,410, 4,741,779, 4,775,585, 4,906,466, 4,911,898, 4,911,899, 4,938,955, 4,938,958, 5,503,840, 5,180,585, 5,556,699, 5,595,750, 6,071,542, incorporated herein by reference in their entirety.

Such zeolites have been incorporated in antibiotic resins (as shown in U.S. Pat. Nos. 4,938,955 and 4,906,464) and polymer articles (U.S. Pat. No. 4,775,585) while other uses are described in U.S. Pat. Nos. 5,714,445; 5,697,203; 5,562,872; 5,180,585; 5,714,430; and 5,102,401, all incorporated herein by reference in their entirety.

In the antibiotic film of this invention, either natural or synthetic zeolites may be used as the "zeolite component". Zeolites are aluminosilicates, of either natural or synthetic origin, which have sites at which cationic exchange may occur. By treating them with solutions of metal ions, a desired antimicrobial metal ion can be substituted in the zeolite structure.

Zeolite is generally aluminosilicate having a three dimensionally grown skeleton structure and is generally represented by $XM_{2/n}$—$Al_2O_3$—$YSiO_2$—$ZH_2O$, written with $Al_2O_3$ as a basis, wherein M represents an ion-exchangeable metal ion, which is usually the ion of a monovalent or divalent metal; n corresponds to the valence of the metal; X is a coefficient of the metal oxide; Y is a coefficient of silica; and Z is the number of water of crystallization. There are known various kinds of zeolites having different component ratios, fine pore diameters, and specific surface areas. As the zeolite used in the present invention, any natural or synthetic zeolites can be used.

Examples of natural zeolite include analcime, chabazite, clinoptilolite, erionite, faujasite, mordenite, and phillipsite. On the other hand, typical examples of synthetic zeolite include A-type zeolite, X-type zeolite, Y-type zeolite, and mordenite. A synthetic zeolite is preferably used as the zeolite in the present invention. As already mentioned above, the antibiotic zeolites as used herein are those of which ion-exchangeable ions such as sodium ions, potassium ions, calcium ions, magnesium ions and iron ions are partially or completely ion-exchanged with the aforementioned antibiotic metal ions such as silver, copper or zinc ions or mixtures thereof.

The shape of zeolite may preferably be powdery particulate. A particle size of the zeolite can suitably be selected depending on application. For films of the present invention, the average particle size is generally 10 microns or less, preferably the average particle size is 6 microns or less, more preferably the average particle size is 5 microns or less. For films of the present invention, the average particle size is generally 0.1 microns or more, preferably the average particle size is 0.2 microns or more, more preferably the average particle size is 0.5 microns or more.

The metal is preferably supported on solid particles of zeolite through an ion-exchange reaction. Zeolite is preferably ion-exchanged with metal ions in an amount of less than an ion-exchangeable amount of the zeolite particles, particularly in an amount less than about 100%, preferably in an amount less than about 90%.

It should be understood that the amount of the metal incorporated in the metal-zeolite might vary depending upon the metal used and whether or not combinations of metals are used. In the case of silver alone, the amount of the metal incorporated in the metal-zeolite is generally 20% by weight or less, preferably from about 0.001 to about 15% by weight, more preferably from about 0.01 to about 10% by weight, most preferably from about 0.05 to about 5% by weight, based on anhydrous zeolite plus metal.

In the case of zinc or copper, the amount of zinc or copper incorporated in the metal-zeolite is generally 25% by weight or less, preferably from about 0.001 to about 20% by weight, more preferably from about 0.01 to about 15% by weight, most preferably from about 0.05 to about 10% by weight, based on anhydrous zeolite plus metal. It is possible to use two or more of silver, copper, zinc and the other metal ions together. In this case, although the total amount of the metal ions is dependent on the composition of the metal ions, it is generally 25% by weight or less, preferably from about 0.001 to about 20% by weight, more preferably from about 0.01 to about 15% by weight, most preferably from about 0.05 to about 10% by weight, based on anhydrous zeolite plus metal.

It is possible to also incorporate other ions than the antibacterial metal ions, for example, sodium, potassium, magnesium, calcium, aluminum, titanium, cerium and other metal ions. Accordingly, these ions may remain or co-exist.

After drying, the antibiotic zeolites thus obtained are pulverized and classified and then are incorporated into a desired resin.

b. Polymers

The metal coating compositions are generally based on aminoalkyd resins, aminoacrylic resins, epoxy resins, and polyurethane resins. In the present invention, the organic polymeric materials used for forming antibiotic-containing films may be any synthetic, natural or semi-synthetic organic polymers so far as they can be formed into films. Generally, such polymers are thermoplastic polymers or thermoset polymers. Examples of such organic polymeric materials include, but are not limited to, acetate rayon, acrylic resins, acrylonitrile-butadiene-styrene (ABS) resins and acrylic resins, aliphatic and aromatic polyamides, aliphatic and aromatic polyesters, allyl resin, (Allyl), AS resins, butadiene resins, chlorinated polyethylene, conductive resins, copolymerised polyamides, copolymers of ethylene and vinyl acetate, cuprammonium rayons and natural and synthetic rubbers, EEA resins, epoxy resins (e.g., bisphenol, dihydroxyphenol, and novolak), ether ketone resins, ethylene vinyl alcohol, (E/VAL), fluorine resins, fluorocarbon polymers, fluoroplastics, (PTFE), (FEP, PFA, CTFE, ECTFE, ETFE), high density polyethyelenes, ionomer resins, liquid crystal polymer, (LCP), low density polyethylenes, melamine formaldehyde, (melamine resins), natural polymers such as cellulosics, nylons, phenol-formaldehyde plastic, (PF) phenolic resins, polyacetal, (acetal), polyacrylates, (acrylic), polyacrylonitrile, (PAN), (acrylonitrile), polyamide, (PA), (nylon), polyamide-imide, (PAI), polyaryletherketone, (PAEK), (ketone), polybutadiene, (PBD), polybutylene terephthalate, polybutylene, (PB), polycarbonate, (PC), polycarbonates, polydicyclopentadiene, (PDCP), polyketones, (PK), polyester block copolymers, polyesters, polyesterurethane, polyesterurethaneurea, polyether and polyester block polymers, polyether ketoneketone (PEKK), polyetherether ketone (PEEK), polyetherimide, (PEI), polyethers, polyethersulfone, (PES), polyetherurethane, polyetherurethaneurea, polyethylene isophthalate, polyethylene terephthalate, polyethylene, (PE), polyethylenechlorinates, (PEC), polyglycolic acid, polyhexamethylene terephthalate, polyimide, (PI), polylactic acid, polymethylpentene, (PMP), poly-m-phenylene isophthalamide, polyolefins, polyphenylene oxide, (PPO), polyphenylene sulfide, (PPS), polyphthalamide, (PTA), poly-p-phenylene terephthalamide, polypropylene, (PP), polysiloxanes such as polydimethyl siloxane, polystyrene, (PS), polysulfides, polysulfone, (PSU), polytetrafluoroethylene, polyurethane, (PU), polyvinyl acetate, polyvinyl alcohols, polyvinylchloride, (PVC), polyvinylidene chloride, (PVDC), polyvinylidene fluoride and polyvinyl fluoride, rayon, reconstituted silk and polysaccharides, reinforced polyethylene terephthalate resins, segmented polyurethane elastomers, silicone resins, spandex or elastane elastomers, styrene type specific resins, thermoplastic polyurethane elastomers, thermosetting synthetic polymers such as phenol-formaldehyde copolymer, triacetate rayon, unsaturated polyester resins, urea resins, urethane resins, vinyl chloride resins, vinyl polymers, and vinylidene chloride resins. This group includes reasonable copolymers, terpolymers and mixtures of the species listed.

The polymer can be dissolved in suitable solvents or in some cases, dispersed in a suitable liquid or solvent mixture. This may include water. Examples of organic solvents include toluene, xylene, methyl ethyl ketone, methyl isobutyl ketone, ethyl acetate, butyl acetate, cyclohexanone, cyclohexanol, and mixtures thereof. In accordance with the invention, any suitable polymer may be selected by one skilled in the art which is capable of functioning as a matrix for the antimicrobial agents used (and other optional ingredients) and coating the specified sheet metals. It is evident that depending on the particular application or use and other pertinent considerations, an appropriate choice of polymer can readily be made.

The organic polymer acts as a carrier and matrix for the oxides and zeolites further described herein and also as a protective barrier coating for the sheet metal substrates.

Admixing the antibiotic zeolite and an organic polymeric compound in a usual manner and then coating the mixture obtained onto the metallic sheet (forming it into films) can produce the coated products of the present invention. The formation of the film can be carried out according to any known methods for roll coating polymer coatings.

Solvents (or liquids to disperse the polymer) which are useful in accordance with the invention include but are not limited to aliphatic hydrocarbons, aromatic solvents, alcohols and other oxygenated solvents, substituted hydrocarbons, phenols, substituted aromatic hydrocarbons and halogenated aliphatic hydrocarbons. Each resin system has a group of solvents and diluents compatible with the resin and suitable for film forming. In some cases the organic solvent is only used to disperse the resin powder. It is contemplated that water can be used as solvent/diluent or dispersant for some resin compositions.

The polymer coatings according to the present invention may contain other additives as well as antimicrobial compositions. They may contain, for example, polymerization catalysts, stabilizers, delustering agents, optical whitening agents, organic or inorganic pigments, inorganic fillers, plasticisers and so on. It is also possible that the antimicrobial particles themselves can fulfill a dual role and provide the benefits of some of the aforementioned additives.

To the present antibacterial zeolite may be added white pigments such as magnesium oxide, calcium oxide, aluminum oxide, zinc oxide, titanium dioxide, silicon dioxide, calcium carbonate, magnesium carbonate and barium sulfate. In addition, to the present antibacterial oxide or zeolite may be added additives such as magnesium silicate, aluminum silicate, zinc silicate, silica gel-zinc, synthetic hydrotalcite, aluminum tripolyphosphate.

Conventional procedures for incorporating powders in polymer compositions may be used to prepare the polymer articles of the invention. The antimicrobial powders may be added to a monomer or to an intermediate product prior to polymerization. However, generally they are mixed or compounded with a finished polymer before it is applied as a film. Precoating of antimicrobial particles with polymer greatly facilitates incorporation of the particles in the bulk polymer. This may be done, for example, by slurrying the antimicrobial powder with a solution of the polymer, then removing the solvent by drying. From about 0.1 to about 10% by weight of polymer based on the coated powder and preferably from about 0.5 to about 5% by weight of polymer based on the coated powder is suitable for this purpose.

In another embodiment, the coating is placed onto a metal sheet wherein the coating composition is comprised of dispersed epoxy resin particles. Preferably, the metal sheet treated with an epoxy pretreatment is stainless steel or aluminum. The epoxy resin may be a solid or liquid epoxy resin. Preferably the epoxy resin is a liquid that is dispersed (i.e., emulsified) within the solvent. Exemplary epoxy resins include diglycidyl ether of bisphenol A, such as those available from The Dow Chemical Company, Midland, Mich. under the trade name D.E.R., and from Shell Chemical Company, Houston, Tex. under the trade name EPON or EPI-REZ and phenol and cresol epoxy novolacs, such as those available under the trade name D.E.N. from The Dow Chemical Company, Midland, Mich. Other examples of useful epoxy resins include those described in U.S. Pat. Nos. 5,118,729, 5,344,856 and 5,602,193, each incorporated herein by reference. The amount of epoxy resin in the coating composition may be any amount sufficient to coat a metal substrate that, subsequently, can be cured to form a corrosion resistant coating on the metal.

The epoxy coating composition may also contain a surfactant that forms an epoxy resin in water dispersion, wherein the epoxy resin molecules have a neutral or positive surface charge, the surfactant being a nonionic surfactant, amphoteric surfactant or mixture thereof. The nonionic surfactant may be, for example, a nonionic surfactant or combination of surfactants known to form oil in water emulsions. Exemplary nonionic surfactants include polyglycol ether of an epoxy, an alcohol, fat, oil, a fatty acid, a fatty acid ester or an alkylphenol. Exemplary amphoteric surfactants include those known in the art, such as alkyl betaines and dihydroxyethyl glycinates.

The amount of surfactant present in the coating composition may be any amount sufficient to disperse the epoxy resin and cause the epoxy resin particles in the dispersion to have a neutral or positive charge. Generally, the amount of surfactant is at least about 0.1 percent by weight, preferably is at least about 0.5 percent by weight. Generally, the amount of surfactant is at most about 10 percent, preferably is at least about 5 percent by weight of the total coating composition weight.

The epoxy coating composition optionally also contains a latent curing agent. Examples of latent curing agents include dicyandiamide and blocked isocyanates, such as an alcohol-blocked toluene diisocyanate. Preferably the latent curing agent is dicyandiamide. The amount of latent curing agent is an amount sufficient to cure the epoxy resin and generally should be an amount that is not so great that the coating, after curing, fails to provide improved corrosion resistance of a metal substrate. Generally, the amount of latent curing agent is at least about 0.1 percent by weight, preferably is at least about 0.5 percent by weight. Generally, the amount of latent curing agent is at most about 10 percent, preferably is at least about 5 percent by weight of the total coating composition weight.

The aqueous epoxy coating composition, of course, contains water in an amount sufficient, for example, to provide an epoxy in water emulsion when the epoxy is a liquid. The water should also be sufficiently pure to provide a water matrix that fails to cause coagulation of the particles (e.g., epoxy or filler particles) due, for example, to impurities (e.g., ionic impurities).

c. Additional Additives

The polymer film compositions of the present invention may be clear or may contain pigment particles or dyes. The pigment particles are preferably titanium dioxide, alumina or silica. Preferably, pigment particles are titanium dioxide particles are from about 0.1 to about 10 microns in median particle size, preferably from about 0.2 to about 5 microns in median particle size.

The coating may further be comprised of fillers that impart, for example, opacity or improved wear resistance to the coating composition after it has been cured. Exemplary fillers include ceramic particles or whiskers and known surface treated metal pigments. Preferably the filler is a ceramic selected from the group consisting of oxides, borides, nitrides, carbides, hydroxides, carbonates, silicides, silicates and alloys thereof.

When the coating composition contains the filler, the filler is generally present in an amount of about 1 percent to about 50 percent by weight of the total coating composition weight. Preferably the amount of the filler, when present, is at least about 2 percent, more preferably at least about 5 percent. Preferably the amount of the filler, when present, is at most about 40 percent, more preferably at most about 35 percent.

If desired, the coating composition may also contain a cross-linking catalyst, for example, to increase the rate of cross-linking (i.e., cure) of the epoxy at a temperature. Generally, the catalyst may be, for example, a tertiary amine or imidazole. Examples of the catalyst that may be employed in the coating composition include 2-methylimidazole, benzyldimethylamine, dimethyl aminomethyl phenol and tris(dimethylaminomethyl)phenol. Preferably the catalyst is 2-methylimidazole.

When the coating composition contains the catalyst, the catalyst is generally present in an amount of about 0.001 percent to about 1 percent by weight of the total coating composition weight. Preferably the amount of the catalyst, when present, is at least about 0.002 percent, more preferably at least about 0.005 percent and most preferably at least about 0.01 percent to preferably at most about 0.7 percent, more preferably at most about 0.5 percent and most preferably at most about 0.3 percent by weight of the total weight of the coating composition.

If necessary or desired, the coating composition may also contain a small amount of defoamer. The defoamer may be any suitable defoamer, such as those known in the art.

Exemplary defoamers include siloxane-based defoamers. The defoamer, when present, is present only in a quantity necessary to control the foaming of the coating composition, since it has been found that, in general, the defoamer impedes the adherence of the coating composition to a metal substrate. The amount of defoamer, when present, is generally present in an amount of at most about 0.15 percent, more preferably at most about 0.05 percent and most preferably at most about 0.02 percent by weight of the total weight of the coating composition.

4. Coating Application

The pretreated metal sheet is then coated with an antimicrobial polymer composition that includes inorganic antimicrobial particles dispersed in an organic polymer. Exemplary coating polymers are the epoxies, polyvinyl chloride, acrylics, polyurethanes, fluorocarbons, and polyesters. The suitable epoxies include phenolic-modified epoxies, polyester-modified epoxies, epoxy-modified polyvinyl chloride, epoxy melamines and cross-linkable epoxies.

Figure 3:
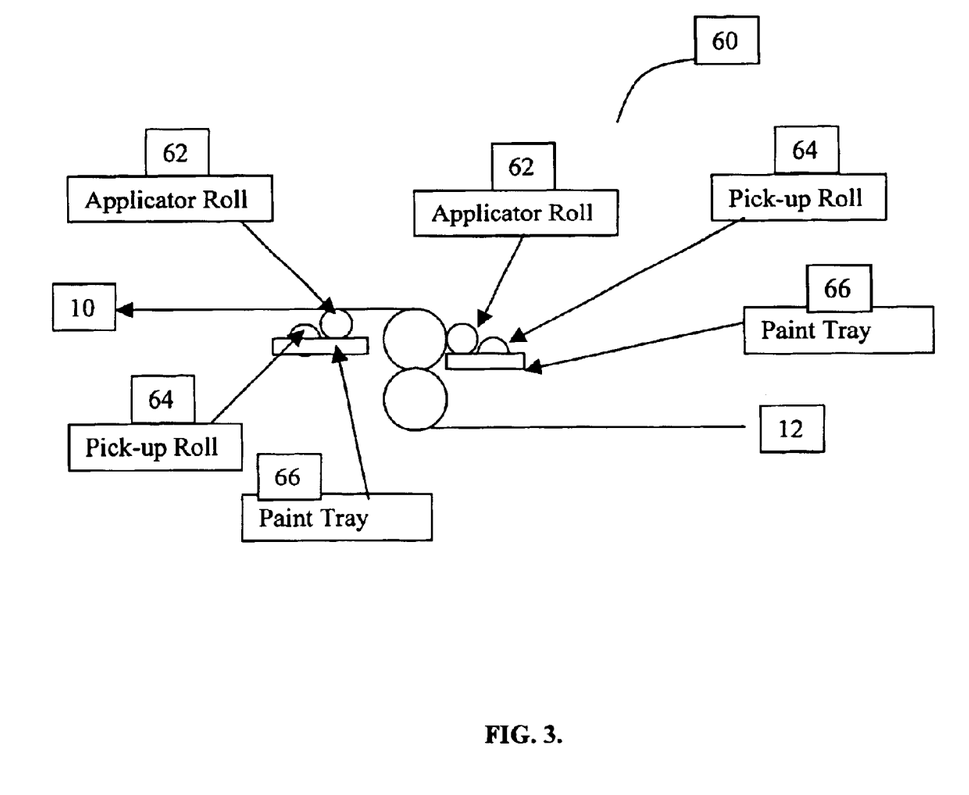
FIG. 3 shows a roll coater or apparatus as an example of the coating apparatus used in the present invention.

A conventional roll coater apparatus 60 as known in the art applies the coating to the substrate 12. In one embodiment, as depicted in FIG. 3, roll coaters may be used to coat both of the substrate 12 surfaces. Optionally, only one surface may be coated. Preferably, the roll coater is a two-roll coater as illustrated in FIG. 3, utilizing a pick-up roll 64 that is fed liquid polymer from a paint tray 66 and transfers the liquid to an applicator roll 62. The applicator roll 62 applies and smoothes the liquid onto the substrate 12 surface. In another embodiment, the sheet may be coated in more than one application to the same sheet in order to provide additional thickness to the final coating. Such multiple coatings may have additional washing, drying and curing stages associated with each coating.

Optionally, the substrate is heated, at least one surface, at the time of application and/or subsequently to a temperature equal to or above the temperature needed to cure the coating and below the substrate outgassing and/or degradation temperature, so that the coating sufficiently flows and forms a smooth continuous coating film, and then cures to a thermoset state or dried to a thermoplastic state without degrading the substrate.

Heating can be performed in infrared, convection ovens, induction or a combination, although convection ovens are preferred. Time and temperature of the final cure will vary somewhat depending on the coatings employed and conditions of use. However, regardless of cure time and temperatures employed, provided that the liquid coating ingredients have been sufficiently flowed onto the substrate before curing, the coating films generated on the substrates will have a visually consistent appearance and will be without entrapped bubbles that interfere with the aesthetic appearance and distinctness of image required by conventional standards.

Referring to FIG. 2, reference numeral 100 generally refers to a coating line incorporating the invention. A metal strip 12 such as annealed cold reduced steel is passed directly from the manufacturing of a strip or is unwound from a coil on an uncoiler by drive rollers. After surface treating, the strip 12 is horizontally passed through a roll coater 60 where liquid polymer is deposited onto the top and/or bottom surface of strip 12. It will be understood that strip 12 also could be vertically passed through coater 60. After being coated with a liquid, strip 12 is passed through a hardening device 70 (e.g., a convection oven) wherein the powder is at least partially hardened by drying or curing. Optionally, after the flowing and/or curing is completed, the coating may be cooled rapidly to form a tightly adherent coating by passing the coated strip through an air or liquid quench, such as water (not shown). The quenched strip can then be dried by a dryer (not shown), such as a pair of air knives for blowing the water from strip 12. Coated strip 10 then may be cut into lengths by a shear or rewound into a coil by a coiler.

Coating line 100 optionally may include a pair of opposing presses, a cleaner, or a preheater. After surface pretreatment 50, strip 12 may be preheated e.g., by passing through an induction heater.

Generally, the content of the antimicrobial metal containing particles in the final coating ranges from about 0.2 to about 30 weight percent based on the final, dried film weight of the coating. This is also on a weight percent based on the weight of the total solids of the applied coating (prior to the evaporation of solvent). The content of the antimicrobial particles in the final coating of the present invention is preferably at least about 0.5 weight percent, more preferably at least about 2 weight percent, and most preferably at least about 5 weight percent based on the final, dried film weight of the coating. The content of the antimicrobial particles in the final coating of the present invention is preferably at most about 25 weight percent, more preferably at most about 20 weight percent, and most preferably at most about 15 weight percent based on the final, dried film weight of the coating.

When coating a metal substrate with the coating composition of the present invention, the coating composition is applied to the metal using any suitable technique, such as blade coater method, gravure coater method, beat coater method, roll coater method, curtain flow coater method, dip coater method, and spray coater method, spin coating, brushing, and electro-deposition. The applied coating should cover the area of the metal substrate that is desired to be coated.

In an alternate embodiment, the metal sheet is coated in more than one application using at least two different types of coatings. In one exemplary method, the first application is a paint or polymer coating without antimicrobial oxide or zeolite additives. At least the final coating application is a polymer coating containing antimicrobial oxide or zeolite additives. The first layer can be used to impart either additional thickness of the total coating, to minimize the total amount of antimicrobial oxide or zeolite additives necessary to coat a given sheet (since only the top surface must have these additives), or to impart other characteristics as known in the art, e.g., additional corrosion resistance coatings, additional or alternative colorants, improved hardness, weather resistance, chemical resistance and other properties.

5. Coat Curing, Drying or Setting

After a coating composition is applied, the coating is at least partially cured or dried to harden and adhere the coating to the metal sheet. The curing is by means suitable to the polymer composition used. Curing can be by heating, infrared radiation, fluorescent radiation, ultraviolet radiation, gamma or beta radiation, X-ray radiation, or combinations thereof. In an exemplary method, the sheet, immediately after coating, is passed through a gas-fired heating zone where solvents are evaporated and the resin is cured or dried. Preferably, the polymer is at least partially cured by heat. Heat curing is to raise the temperature of the coating to accelerate cross-linking reaction. Heat curing can be by various heating means such as an electric heating oven, hot air heating oven, infrared heating oven, and high-frequency heating oven. For curing, a heating temperature and time are properly selected in consideration of the formulation of a coating composition, the size and gage of sheet metal, the capacity of an oven, and other factors. The particular temperature is dependent on such things as the particular epoxy, curing agent and catalyst employed and curing time desired. The temperature, however, should not be so great that the cured coating is degraded, for example, by decomposing. Generally, the drying or curing treatment is carried out under normal pressure or reduced pressure at a temperature of at least about 50° C. to at most about 400° C. Preferably the peak metal temperatures (PMT) for the coated metal sheets is at least about 100° C., more preferably at least about 150° C. and most preferably at least about 200° C. Preferably the peak metal temperatures (PMT) for the coated metal sheets is at most about 350° C., more preferably at most about 300° C. and most preferably at most about 275° C.

The time at the temperature of cure can be any practicable time and is desirably as short as practical. Generally, the time at the curing temperature is at least about 0.1 minute to at most about 24 hours. Preferably the time at the cure temperature is at least about 10 minutes, more preferably at least about 5 minutes and most preferably at least about 0.5 minute. Preferably the time at the cure temperature is at most about 2 hours, more preferably at most about 1 hour and most preferably at most about 0.5 hour. As well within the knowledge of those skilled in the art, the temperature and time are in a relative relationship and also the conditions vary depending on the properties of coating required.

Immediately after heating to cure or dry the coating, the coated metal sheet may then be subjected to quenching in order to harden the coating prior to the final coiling of the sheet product. The quenching can be by any suitable means as known in the art such as by water or other coolant immersion, spray, or mist or by cold air. The coated metal sheet is then typically coiled by conventional means in metal coils.

The thickness of the coating of the present invention is preferably in the range of from about 0.5 to about 30 microns. Preferably thickness of the coating is at least about 2 microns, more preferably at least about 3 microns and most preferably at least about 4 microns. Preferably the thickness of the coating is at most about 20 microns, more preferably at most about 15 microns and most preferably at most about 10 microns.

After curing, the applied coating composition, a metal sheet having a cured resin coating adhered thereto is formed generally having antimicrobial properties. Also, the coating that is formed, typically, has improved fingerprint resistance. The coating also protects the surface from staining when tested against kitchen spills such as ketchup, mustard and pickle juice.

Generally, a silver-bearing refractory compound is incorporated into a polyester or epoxy film coating to control the growth of harmful bacteria, mold and mildew. These film coatings may be economically applied to stainless or carbon steel products on full size production coils by means of roll coating. The antimicrobial properties may last for years depending on the intended application. Clear or pigmented film coatings can be used.

Preferably, silver ions are encapsulated within a zeolite refractory. The zeolite powder is blended into either a polyester or epoxy resin. A thin film coating, about 0.00025" thick, is applied to either a carbon or stainless steel sheet. The silver ions have great mobility and can diffuse to the surface of the steel to inhibit the growth of bacteria and mold.

Silver has long been recognized for its safe antimicrobial properties. Coated products may be effective against many common food borne pathogens such as *Escherichia coli*, *Salmonella* and *Listeria* monocytogenes as well as various types of mold including *Aspergillus niger*.

On metals, such as stainless steels, the zeolite refractory compound, when added to a clear resin coating, hides fingerprints due to the light scattering influence of the micron-scale diameter zeolite particles contained within the coating matrix. The resin coating also protects the surface from staining when tested against kitchen spills such as ketchup, mustard and pickle juice.

EXAMPLE 1

Hot dipped galvanized steel (G-60, carbon steel having a zinc coating of about 0.6 oz. zinc/ft$^2$) with a thickness of 0.045" and a width of 58.00" is run though the roll coating process at a line speed of about 250 fpm. The steel strip is cleaned using an alkaline cleaner (PARCO CLEANER 1200) of potassium hydroxide at about 1 to about 2% concentration, dwell time of about 3 to about 10 seconds, and at a temperature of from about 150 to about 160° F. The steel strip is then rinsed with a water rinse for about 2 to about 4 seconds at about 100° F.

The steel strip is then treated with a chemical conditioning rinse of PARCOLENE AT sodium phosphate compound with titanium, at about 1 to about 1.5 lb per 100-gallon water, for a time from about 2 to about 5 seconds, at a temperature of about 130 F.

The steel strip is then treated with a zinc phosphate pretreatment using Parker BONDERITE 1421 phosphoric acid based solution containing nickel and fluoride additives, for a time about 5 to about 10 seconds, with about 150 to about 250 mg/sq ft coating weight, at a temperature of about 140 to about 150 F. The strip is then rinsed with a clear water rinse for about 2 to about 4 seconds at about 100 F.

The steel strip is then treated with a chrome rinse post-treatment of Parcolene 62 applied at a concentration of 2% in water, composed of chromic acid, hydrofluoric acid and zinc chromate, for an exposure time of about 2 to about 5 seconds, at a pH of about 3.2 to about 3.7, at a temperature of about 120 F.

By means of a roll coater, the strip is then coated with PPG's 1HC5692 polyester melamine containing antimicrobial ZEOMIC powder (Sinanen Co., Inc., Japan). The liquid film coating is applied by means of a conventional two roll coating system and utilizes one pick-up roll per side in contact with each applicator roll. The direction of the applicator roll is opposed to the direction of the strip movement. This is referred to as reverse roll coating.

The metal sheet is cured in an oven to a Peak Metal Temperature of about 440 F, producing a clear, polyester coating, with about 7 Wt-% silver zeolite, based on dried coating, with a coating thickness of from about 0.2 to about 0.3 mils, dry film thickness.

Adhesion as measured with 2 T bend-test was excellent, as were the results of Olsen dome tests. Subsequent efficacy tests conducted using *E. coli* bacteria indicated more than a 3 log reduction in a 24 hour period relative to the initial inoculation levels.

EXAMPLE 2

Stainless steel strips, Type 304, at thicknesses of about 0.02", 0.030", 0.036", 0.048", 0.060", 0.075", all with a width of about 50", are run through the roll coating process at a line speed of about 0.024"@300 fpm, 0.030"@300 fpm, 0.036"@325 fpm, 0.048"@275 fpm, 0.060"@225 fpm, 0.075"@175 fpm.

The steel strip is cleaned using an alkaline cleaner (PARCO CLEANER 1200) of potassium hydroxide based, at about 1 to about 2% concentration, dwell time of about 3 to about 10 seconds, and at a temperature of from about 150 to about 160° F. The steel strip is then rinsed with a water rinse for about 2 to about 4 seconds at about 100° F.

By means of a roll coater, the strip is then coated with PPG's Nupal 510R Pretreatment, a water based phosphatized epoxy with propylene glycol monomethyl ether. Nupal is applied from a solution at ambient temperature, with a dwell time of about 1 second, and a coating weight of 10 mg/sq ft. The Nupal coating is then dried with warm air. The antimicrobial coating used for stainless steel is PPG's 1HC5794 epoxy melamine containing antimicrobial ZEOMIC powder (Sinanen Co., Inc., Japan).

After coating, the sheet passes through a gas fired heating zone where the solvents are evaporated and the resin is cured or dried to a Peak Metal Temperature (PMT) of about 460 F, water quenched to a metal temperature of about less than 150 F, producing a clear, epoxy coating, with about 7 Wt-% silver zeolite, based on dried coating, with a coating thickness of from about 0.2 to about 0.3 mils, dry film thickness.

Results indicated that the coating had excellent adhesion as seen by passing a 1 T bend test. The coating hardness was measured as 5H pencil. MEK rubs were found to be in the range of 5–10. Efficacy test results were similar to those reported in Example 1.

EXAMPLE 3

Same as above with the following parameters:

Stainless steel strip, Type 304, at thickness of about 0.035", a width of about 37.50", is coated at a line speed of about 275 fpm. The metal is first cleaned with an alkaline cleaner at about 150° F. using about 40 to about 60 psi spray.

By means of a roll coater, the strip is then coated with PPG's Nupal 510R Pretreatment, a water based phosphatized epoxy with propylene glycol monomethyl ether. Nupal is applied from a solution at ambient temperature, with a dwell time of about 1 second, and a coating weight of 10 mg/sq ft. The Nupal coating is then dried with warm air.

After coating, the sheet passes through a gas fired heating zone where the solvents are evaporated and the resin is cured or dried to a Peak Metal Temperature of about 490 F, water quenched to a metal temperature of less than about 150 F, producing a clear, epoxy coating, with about 7 Wt-% silver zeolite, based on dried coating, with a coating thickness of from about 0.2 to about 0.3 mils, dry film thickness.

The coating has a hardness of 5H, MEK rubs of >120, and a bend test of 1 T without coating loss. The higher PMT versus Example 2 resulted in higher MEK rubs and a more complete cure. Efficacy results were similar to Example 1.

EXAMPLE 4

Same as above with the following parameters:

Hot dipped galvanized steel, G-60, with a thickness of 0.024" and a width of 60.00" is run through the roll coating process at a line speed of about 300 fpm. The steel strip is cleaned using an alkaline cleaner at a temperature of about 150° F. using about 40 to about 60 psi spray.

The steel strip is then treated with a chemical conditioning rinse of PARCOLENE No. 62, at a temperature of about 120 F. The steel strip is then treated with a zinc phosphate pretreatment using Parker BONDERITE 1421 phosphoric acid based solution.

By means of a roll coater, the strip is then coated with a blue-pigmented epoxy containing antimicrobial ZEOMIC powder (Sinanen Co., Inc., Japan). The liquid film coating is applied by means of a conventional two roll coating system and utilizes one pick-up roll per side in contact with each applicator roll.

The metal sheet is cured in an oven to a Peak Metal Temperature of about 490 F, water quenched to a metal temperature of about less than about 150 F, producing a blue, epoxy coating, with about 7 wt-% silver zeolite, based on dried coating, with a coating thickness of from about 0.2 to about 0.3 mils, dry film thickness.

The coating hardness of 3H, MEK rubs of >75, and a bend test of 2 T without coating loss indicated excellent physical properties were obtained. Efficacy results were similar to those of Example 1.

EXAMPLE 5

Coating Characteristics: A thin, about 0.20 to about 0.30 mil, coating film may be readily applied by liquid roll coating. When a #4 polished stainless steel surface is coated; the surface roughness is reduced from approximately 31 microinches in the transverse direction to approximately 11 microinches. In the longitudinal direction, roughness averages increases from about 6 to about 11. The coating fills the grooves within the polished surface decreasing roughness values in the transverse direction and increasing roughness values in the longitudinal direction of the steel. Thus, a more uniform surface roughness profile is maintained after liquid roll coating with the antimicrobial compound added to the epoxy resin coating. A #4 polished stainless steel is most often used in restaurant and in high-end kitchen appliances. A Type 304 stainless steel is the most common grade for these applications.

Surface Roughness, Microinches, Average Values
Type 304 Stainless Steel, Decorative Polished Finish

|  | #4 Polished, Uncoated | #4 Polished, Coated |
|---|---|---|
| Ra, Transverse | 31 | 11 |
| Ra, Longitudinal | 6 | 11 |

Stainless polished steel finishes, when coated with the antimicrobial compound, tend to hide fingerprints and make the surface have a lower relative gloss finish compare to uncoated, standard polished surfaces. Gloss measurements for representative stainless Type 304 polished and polished and then coated surfaces are presented in the table below. The angle of illumination is 20° from the normal to the surface.

TABLE 1

|  | #4 Polished, Uncoated | #4 Polished, Coated |
|---|---|---|
| Gloss, Transverse | 39 | 28 |
| Gloss, Longitudinal | 74 | 40 |

Stainless polished finishes, when coated with the clear, epoxy resin that contains the antimicrobial compound tends to be nondirectional with respect to surface roughness and gloss compared to the conventional polished finishes. This coating yields a more uniform and blemish-free surface.

EXAMPLE 6

Efficacy testing was performed on both carbon and stainless steel products that had been coated with resins containing 7 wt % of the antimicrobial compound, AgION. These products were tested as follows against two of the most common food borne pathogens, *E. coli* and *Listeria*. Results are and the testing protocols for this work are presented below:

Organisms. *Escherichia coli* and *Listeria monocytogenes*

Preparation of test samples. Coupons (2"×2") of stainless steel, both entirely bare and entirely AgION-coated, and galvanized steel, coated on one side only with AgION. Coupons were cleaned by swabbing, both sides, and all cut edges with 70% ethanol. Coupons were propped in sterile empty petri dishes and allowed to air-dry.

Bacterial exposure to steel coupons. Petri dishes were closed and incubated at 37° C. All experiments were performed in duplicate.

Recovery of bacteria from steel coupons. After bacterial suspensions had been in contact with steel coupons for 24 h, the coupons were inverted into the buffer solution in the bottom of the petri dish. Serial 10× dilutions in PBS were made of the buffer suspension, and plated as described above.

TABLE 2

Effect on bacteria of 24-h exposure to AgION-coated surfaces.[1]

| | *Eseherichia coli* | | *Listeria monocytogenes* | |
|---|---|---|---|---|
| Sample Identification | Zero Contact Time | 24 Hours Contact Time | Zero Contact Time | 24 Hours Contact Time |
| Stainless | $4.0 \times 10^5$ | $3.0 \times 10^6$ | $1.5 \times 10^4$ | $1.0 \times 10^7$ |
| Stainless + AgION | $4.0 \times 10^5$ | <1 | $1.5 \times 10^4$ | <1 |
| Galvanized | $4.0 \times 10^5$ | $3.4 \times 10^6$ | $1.5 \times 10^4$ | $1.5 \times 10^7$ |
| Galvanized + AgION | $4.0 \times 10^5$ | <1 | $1.5 \times 10^4$ | <1 |

[1]All numbers represent colony-forming units
[2]All tests were performed in duplicate; no statistical analysis was performed As shown from the test data, almost all of the bacteria present of the surfaces of treated steel samples are eliminated after the 24 hrs time period. Control steel surfaces exhibited an increase in bacterial counts occurred during the test.

What is claimed is:

1. A process of manufacturing a metal sheet precoated with an antimicrobial polymer coating, comprising:
    providing a metal sheet substrate provided as a continuous strip having two opposed planar surfaces and comprising a nickel alloy base metal selected from the group consisting of nickel manganese, nickel-aluminum, nickel silver, nickel bronze and nickel-silicon;
    cleaning the surface of the substrate with an alkaline solution comprising one or more agents selected from the group consisting of caustic soda, soda ash, alkaline silicates, sodium hydroxide, sodium carbonate, sodium metasilicate, phosphates, alkaline builders, ammonium acid phosphate, ammonium hydroxide, monoethanol amine, and dimethylamine oxide wherein cleaning comprises removing bulk and molecular organic contaminants;
    pretreating at least one planar surface of the substrate to promote adhesion of a polymer coating;
    applying a polymer coating onto at least one planar surface of the substrate by roll coating the substrate with a polymer containing an anti-microbial powder comprising core particles associated with an antimicrobial metal component;
    wherein the content of the antibiotic powder is in the range of from about 0.2 to about 30 weight percent of the polymeric coating;
    wherein the core particle comprises one or more particles selected from the group consisting of: oxides selected from the group consisting of titanium, aluminum, zinc and copper oxides, sulfates selected from the group consisting of calcium, strontium and barium sulfates, sulfides selected from the group consisting of zinc and copper sulfides, zeolites, zirconium phosphate, mica, talc, kaolin, mullite, silica and mixtures thereof;
    wherein the antimicrobial metal component is selected from the group consisting of silver, copper, zinc, mercury, tin, lead, bismuth, cadmium, chromium, cobalt, nickel, and thallium ions and mixtures thereof; and
    treating the coated substrate to produce at least a partially hardened and adhered antimicrobial coating on the final sheet product.

2. A process of manufacturing a metal sheet precoated with an antimicrobial polymer coating, comprising:
    providing a metal sheet substrate provided as a continuous strip having two opposed planar surfaces and comprising a base metal selected from the group selected from the group consisting essentially of copper alloys, brass, bronze, silicon bronze, silicon brass, nickel silver and nickel bronze;
    cleaning the surface of the substrate with an alkaline solution comprising one or more agents selected from the group consisting of caustic soda, soda ash, alkaline silicates, sodium hydroxide, sodium carbonate, sodium metasilicate, phosphates, alkaline builders, ammonium acid phosphate, ammonium hydroxide, monoethanol amine, and dimethylamine oxide wherein cleaning comprises removing bulk and molecular organic contaminants;
    pretreating at least one planar surface of the substrate to promote adhesion of a polymer coating;
    applying a polymer coating onto at least one planar surface of the substrate by roll coating the substrate with a polymer containing an anti-microbial powder comprising core particles associated with an antimicrobial metal component;
    wherein the content of the antibiotic powder is in the range of from about 0.2 to about 30 weight percent of the polymeric coating;
    wherein the core particle comprises one or more particles selected from the group consisting of: oxides selected from the group consisting of titanium, aluminum, zinc and copper oxides, sulfates selected from the group consisting of calcium, strontium and barium sulfates, sulfides selected from the group consisting of zinc and copper sulfides, zeolites, zirconium phosphate, mica, talc, kaolin, mullite, silica and mixtures thereof;
    wherein the antimicrobial metal component is selected from the group consisting of silver, copper, zinc, mercury, tin, lead, bismuth, cadmium, chromium, cobalt, nickel, and thallium ions and mixtures thereof; and
    treating the coated substrate to produce at least a partially hardened and adhered antimicrobial coating on the final sheet product.

3. A process of manufacturing a metal sheet precoated with an antimicrobial polymer coating, comprising:

providing a metal sheet substrate having two opposed planar surfaces comprising a base metal selected from the group consisting of aluminum, iron, nickel, titanium, molybdenum, magnesium, manganese, copper, silver, lead, tin, chromium, beryllium, tungsten, cobalt and alloys thereof;

cleaning the surface of the substrate with an alkaline solution comprising one or more agents selected from the group consisting of caustic soda, soda ash, alkaline silicates, sodium hydroxide, sodium carbonate, sodium metasilicate, phosphates, alkaline builders, ammonium acid phosphate, ammonium hydroxide, monoethanol amine, and dimethylamine oxide wherein cleaning comprises removing bulk and molecular organic contaminants;

pretreating at least one planar surface of the substrate to promote adhesion of a polymer coating wherein the pretreating creates a chemical conversion interlayer coating formed by contacting the metal with an aqueous phosphating composition comprising phosphoric acid and a divalent metal ion wherein the composition has a total phosphate content from about 0.01 to about 3 moles/liter and the divalent metal ion is selected from the group consisting of Mg, Ca, Sr, and Ba;

applying a polymer coating onto at least one planar surface of the substrate by roll coating the substrate with a polymer containing an anti-microbial powder comprising core particles associated with an antimicrobial metal component;

wherein the content of the antibiotic powder is in the range of from about 0.2 to about 30 weight percent of the polymeric coating;

wherein the core particle comprises one or more particles selected from the group consisting of: oxides selected from the group consisting of titanium, aluminum, zinc and copper oxides, sulfates selected from the group consisting of calcium, strontium and barium sulfates, sulfides selected from the group consisting of zinc and copper sulfides, zeolites, zirconium phosphate, mica, talc, kaolin, mullite, silica and mixtures thereof;

wherein the antimicrobial metal component is selected from the group consisting of silver, copper, zinc, mercury, tin, lead, bismuth, cadmium, chromium, cobalt, nickel, and thallium ions and mixtures thereof; and treating the coated substrate to produce at least a partially hardened and adhered antimicrobial coating on the final sheet product.

4. A process of manufacturing a metal sheet precoated with an antimicrobial polymer coating, comprising:

providing a metal sheet substrate having two opposed planar surfaces comprising a base metal selected from the group consisting of aluminum, iron, nickel, titanium, molybdenum, magnesium, manganese, copper, silver, lead, tin, chromium, beryllium, tungsten, cobalt and alloys thereof wherein the metal substrate is predominantly galvanized steel or steel;

cleaning the surface of the substrate with an alkaline solution comprising one or more agents selected from the group consisting of caustic soda, soda ash, alkaline silicates, sodium hydroxide, sodium carbonate, sodium metasilicate, phosphates, alkaline builders, ammonium acid phosphate, ammonium hydroxide, monoethanol amine, and dimethylamine oxide wherein cleaning comprises removing bulk and molecular organic contaminants;

pretreating at least one planar surface of the substrate to promote adhesion of a polymer coating wherein the pretreating creates a chemical conversion interlayer coating formed by contacting the metal with an aqueous phosphating composition comprising phosphoric acid and a divalent metal ion wherein the composition has a total phosphate content from about 0.01 to about 3 moles/liter and wherein the phosphating composition includes boric acid in an amount of at least 0.02 moles/liter;

applying a polymer coating onto at least one planar surface of the substrate by roll coating the substrate with a polymer containing an anti-microbial powder comprising core particles associated with an antimicrobial metal component;

wherein the content of the antibiotic powder is in the range of from about 0.2 to about 30 weight percent of the polymeric coating;

wherein the core particle comprises one or more particles selected from the group consisting of: oxides selected from the group consisting of titanium, aluminum, zinc and copper oxides, sulfates selected from the group consisting of calcium, strontium and barium sulfates, sulfides selected from the group consisting of zinc and copper sulfides, zeolites, zirconium phosphate, mica, talc, kaolin, mullite, silica and mixtures thereof;

wherein the antimicrobial metal component is selected from the group consisting of silver, copper, zinc, mercury, tin, lead, bismuth, cadmium, chromium, cobalt, nickel, and thallium ions and mixtures thereof; and treating the coated substrate to produce at least a partially hardened and adhered antimicrobial coating on the final sheet product.

5. A process of manufacturing a metal sheet precoated with an antimicrobial polymer coating, comprising:

providing a metal sheet substrate having two opposed planar surfaces comprising a base metal selected from the group consisting of aluminum, iron, nickel, titanium, molybdenum, magnesium, manganese, copper, silver, lead, tin, chromium, beryllium, tungsten, cobalt and alloys thereof;

cleaning the surface of the substrate with an alkaline solution comprising one or more agents selected from the group consisting of caustic soda, soda ash, alkaline silicates, sodium hydroxide, sodium carbonate, sodium metasilicate, phosphates, alkaline builders, ammonium acid phosphate, ammonium hydroxide, monoethanol amine, and dimethylamine oxide wherein cleaning comprises removing bulk and molecular organic contaminants;

pretreating at least one planar surface of the substrate to promote adhesion of a polymer coating wherein the pretreating creates a chemical conversion interlayer coating formed by contacting the metal with a composition selected from the group consisting of chromium phosphate, chromium chromate, zinc phosphate, iron phosphate, or an epoxy;

applying a polymer coating onto at least one planar surface of the substrate by roll coating the substrate with a polymer containing an anti-microbial powder comprising core particles associated with an antimicrobial metal component wherein the polymer is selected from the group consisting of acrylic resins, polyester resins, polyethylene, polypropylene, epoxy resins, polyurethane resins, olefin resins, polyamide resins, ethylene-vinyl acetate copolymer, ethylene-vinyl alcohol copolymer, polyvinyl chloride, polyvinylidene chloride, polystyrene, ABS resin, polyethylene terephthalate, nylon, polycarbonate and copolymers, terpolymers and mixtures thereof;

wherein the content of the antibiotic powder is in the range of from about 0.2 to about 30 weight percent of the polymeric coating;

wherein the core particle comprises one or more particles comprising a synthetic zeolite selected from the group consisting of A-type zeolite, X-type zeolite, Y-type zeolite, and mordenite having ion-exchangeable ions partially ion-exchanged with antibiotic metal ions in an amount less than about 90% of the ion-exchangeable saturation capacity of the zeolite particles, wherein the ion-exchangeable ions are selected from the group consisting of sodium ions, potassium ions, calcium ions, magnesium ions and iron ions and wherein the antibacterial metals ions are selected from the group consisting of silver, copper, zinc, mercury, tin, lead, bismuth, cadmium, chromium, cobalt, nickel, and thallium ions or mixtures thereof, and wherein the zeolite particles retain the antibacterial metal ions at ionic exchange sites of the zeolite in an amount less than the ion exchange saturation capacity of the zeolite wherein the zeolite is ion-exchanged with one or more additional metal ions selected from the group consisting of silica, silicates, silicon dioxide, borosilicates, aluminosilicates, alumina, aluminum phosphate, zinc, zinc oxide, zinc silicate, copper, copper oxide, and mixtures thereof;

wherein the antimicrobial metal component is selected from the group consisting of silver, copper, zinc, mercury, tin, lead, bismuth, cadmium, chromium, cobalt, nickel, and thallium ions and mixtures thereof; and treating the coated substrate to produce at least a partially hardened and adhered antimicrobial coating on the final sheet product.

6. The process of claim 5 wherein the additional metal ions comprise from about 0.1 to about 20% by weight, based on anhydrous zeolite plus metal.

7. A process of manufacturing a metal sheet precoated with an antimicrobial polymer coating comprising:

providing a metal sheet substrate having two opposed planar surfaces comprising a base metal selected from the group consisting of aluminum, iron, nickel, titanium, molybdenum, magnesium, manganese, copper, silver, lead, tin, chromium, beryllium, tungsten, cobalt and alloys thereof;

cleaning the surface of the substrate with an alkaline solution comprising one or more agents selected from the group consisting of caustic soda, soda ash, alkaline silicates, sodium hydroxide, sodium carbonate, sodium metasilicate, phosphates, alkaline builders, ammonium acid phosphate, ammonium hydroxide, monoethanol amine, and dimethylamine oxide wherein cleaning comprises removing bulk and molecular organic contaminants;

pretreating at least one planar surface of the substrate to promote adhesion of a polymer coating wherein the pretreating creates a chemical conversion interlayer coating formed by contacting the metal with a composition selected from the group consisting of chromium phosphate, chromium chromate, zinc phosphate, iron phosphate, or an epoxy;

applying a polymer coating onto at least one planar surface of the substrate by roll coating the substrate with a polymer containing an anti-microbial powder comprising core particles associated with an antimicrobial metal component wherein the polymer is selected from the group consisting of acrylic resins, polyester resins, polyethylene, polypropylene, epoxy resins, polyurethane resins, olefin resins, polyamide resins, ethylene-vinyl acetate copolymer, ethylene-vinyl alcohol copolymer, polyvinyl chloride, polyvinylidene chloride, polystyrene, ABS resin, polyethylene terephthalate, nylon, polycarbonate and copolymers, terpolymers and mixtures thereof;

wherein the content of the antibiotic powder is in the range of from about 0.2 to about 30 weight percent of the polymeric coating;

wherein the core particle comprises one or more particles comprising a synthetic zeolite selected from the group consisting of A-type zeolite, X-type zeolite, Y-type zeolite, and mordenite having ion-exchangeable ions partially ion-exchanged with antibiotic metal ions in an amount less than about 90% of the ion-exchangeable saturation capacity of the zeolite particles, wherein the ion-exchangeable ions are selected from the group consisting of sodium ions, potassium ions, calcium ions, magnesium ions and iron ions and wherein the antibacterial metals ions are selected from the group consisting of silver, copper, zinc, mercury, tin, lead, bismuth, cadmium, chromium, cobalt, nickel, and thallium ions or mixtures thereof, and wherein the zeolite particles retain the antibacterial metal ions at ionic exchange sites of the zeolite in an amount less than the ion exchange saturation capacity of the zeolite wherein the antimicrobial metal component is selected from the group consisting of silver, copper, zinc, mercury, tin, lead, bismuth, cadmium, chromium, cobalt, nickel, and thallium ions and mixtures thereof;

wherein the antimicrobial powder is additionally coated with a dispersion enhancing coating selected from the group consisting of resin, hydrous metal oxide, and mixtures thereof; and treating the coated substrate to produce at least a partially hardened and adhered antimicrobial coating on the final sheet product.

8. A process of manufacturing a metal sheet precoated with an antimicrobial polymer coating, comprising:

providing a metal sheet substrate having two opposed planar surfaces comprising a base metal selected from the group consisting of aluminum, iron, nickel, titanium, molybdenum, magnesium, manganese, copper, silver, lead, tin, chromium, beryllium, tungsten, cobalt and alloys thereof;

cleaning the surface of the substrate by deoxidizing the surface by immersion in an acid solution, and rinsing in water;

pretreating at least one planar surface of the substrate to promote adhesion of a polymer coating wherein the pretreating creates a chemical conversion interlayer coating formed by contacting the metal with a composition selected from the group consisting of chromium phosphate, chromium chromate, zinc phosphate, iron phosphate, or an epoxy;

applying a polymer coating onto at least one planar surface of the substrate by two-roll roll coating the substrate with a polymer containing an anti-microbial powder comprising core particles associated with an antimicrobial metal component wherein the polymer is selected from the group consisting of acrylic resins, polyester resins, polyethylene, polypropylene, epoxy resins, polyurethane resins, olefin resins, polyamide resins, ethylene-vinyl acetate copolymer, ethylene-vinyl alcohol copolymer, polyvinyl chloride, polyvinylidene chloride, polystyrene, ABS resin, polyethylene terephthalate, nylon, polycarbonate and copolymers, terpolymers and mixtures thereof;

wherein the content of the antibiotic powder is in the range of from about 0.2 to about 30 weight percent of the polymeric coating;

wherein the core particle comprises one or more particles comprising a synthetic zeolite selected from the group consisting of A-type zeolite, X-type zeolite, Y-type zeolite, and mordenite having ion-exchangeable ions partially ion-exchanged with antibiotic metal ions in an amount less than about 90% of the ion-exchangeable saturation capacity of the zeolite particles, wherein the ion-exchangeable ions are selected from the group consisting of sodium ions, potassium ions, calcium ions, magnesium ions and iron ions and wherein the antibacterial metals ions are selected from the group consisting of silver, copper, zinc, mercury, tin, lead, bismuth, cadmium, chromium, cobalt, nickel, and thallium ions or mixtures thereof, and wherein the zeolite particles retain the antibacterial metal ions at ionic exchange sites of the zeolite in an amount less than the ion exchange saturation capacity of the zeolite;

wherein the antimicrobial metal component is selected from the group consisting of silver, copper, zinc, mercury, tin, lead, bismuth, cadmium, chromium, cobalt, nickel, and thallium ions and mixtures thereof; and treating the coated substrate to produce at least a partially hardened and adhered antimicrobial coating on the final sheet product by a method selected from the group consisting of heat, infrared radiation, fluorescent radiation, ultraviolet radiation, gamma or beta radiation, X-ray radiation, or combinations thereof.

9. A process of manufacturing a metal sheet precoated with an antimicrobial polymer coating, comprising:

providing a metal sheet substrate having two opposed planar surfaces comprising a base metal wherein the base metal is a nickel alloy selected from the group consisting of nickel manganese, nickel-aluminum, nickel silver, nickel bronze and nickel-silicon;

cleaning the surface of the substrate wherein cleaning comprises removing bulk and molecular organic contaminants;

pretreating at least one planar surface of the substrate to promote adhesion of a polymer coating;

applying a polymer coating onto at least one planar surface of the substrate by roll coating the substrate with a polymer containing an anti-microbial powder comprising core particles associated with an antimicrobial metal component;

wherein the content of the antibiotic powder is in the range of from about 0.2 to about 30 weight percent of the polymeric coating;

wherein the core particle comprises one or more particles selected from the group consisting of: oxides selected from the group consisting of titanium, aluminum, zinc and copper oxides, sulfates selected from the group consisting of calcium, strontium and barium sulfates, sulfides selected from the group consisting of zinc and copper sulfides, zeolites, zirconium phosphate, mica, talc, kaolin, mullite, silica and mixtures thereof;

wherein the antimicrobial metal component is selected from the group consisting of silver, copper, zinc, mercury, tin, lead, bismuth, cadmium, chromium, cobalt, nickel, and thallium ions and mixtures thereof; and treating the coated substrate to produce at least a partially hardened and adhered antimicrobial coating on the final sheet product.

10. A process of manufacturing a metal sheet precoated with an antimicrobial polymer coating, comprising:

providing a metal sheet substrate having two opposed planar surfaces comprising a base metal selected from the group consisting of aluminum, iron, nickel, titanium, molybdenum, magnesium, manganese, copper, silver, lead, tin, chromium, beryllium, tungsten, cobalt and alloys thereof;

cleaning the surface of the substrate wherein cleaning comprises removing bulk and molecular organic contaminants;

pretreating at least one planar surface of the substrate to promote adhesion of a polymer coating wherein the pretreating creates a chemical conversion interlayer coating formed by contacting the metal with an aqueous phosphating composition comprising phosphoric acid and a divalent metal ion selected from the group consisting of Mg, Ca, Sr, and Ba;

applying a polymer coating onto at least one planar surface of the substrate by roll coating the substrate with a polymer containing an anti-microbial powder comprising core particles associated with an antimicrobial metal component;

wherein the content of the antibiotic powder is in the range of from about 0.2 to about 30 weight percent of the polymeric coating;

wherein the core particle comprises one or more particles selected from the group consisting of: oxides selected from the group consisting of titanium, aluminum, zinc and copper oxides, sulfates selected from the group consisting of calcium, strontium and barium sulfates, sulfides selected from the group consisting of zinc and copper sulfides, zeolites, zirconium phosphate, mica, talc, kaolin, mullite, silica and mixtures thereof;

wherein the antimicrobial metal component is selected from the group consisting of silver, copper, zinc, mercury, tin, lead, bismuth, cadmium, chromium, cobalt, nickel, and thallium ions and mixtures thereof; and treating the coated substrate to produce at least a partially hardened and adhered antimicrobial coating on the final sheet product.

11. A process of manufacturing a metal sheet precoated with an antimicrobial polymer coating, comprising:

providing a metal sheet substrate having two opposed planar surfaces comprising a base metal selected from the group consisting of aluminum, iron, nickel, titanium, molybdenum, magnesium, manganese, copper, silver, lead, tin, chromium, beryllium, tungsten, cobalt and alloys thereof;

cleaning the surface of the substrate wherein cleaning comprises removing bulk and molecular organic contaminants;

pretreating at least one planar surface of the substrate to promote adhesion of a polymer coating;

applying a polymer coating onto at least one planar surface of the substrate by roll coating the substrate with a polymer containing an anti-microbial powder comprising core particles associated with a first and second antimicrobial metal component and wherein the core particles retain the first antibacterial metal ions at ionic exchange sites of the particles;

wherein the content of the antibiotic powder is in the range of from about 0.2 to about 30 weight percent of the polymeric coating;

wherein the core particle comprises one or more particles selected from the group consisting of: oxides selected from the group consisting of titanium, aluminum, zinc and copper oxides, sulfates selected from the group consisting of calcium, strontium and barium sulfates, sulfides selected from the group consisting of zinc and copper sulfides, zeolites, zirconium phosphate, mica, talc, kaolin, mullite, silica and mixtures thereof;

wherein the first antimicrobial metal component is selected from the group consisting of silver, copper, zinc, mercury, tin, lead, bismuth, cadmium, chromium, cobalt, nickel, and thallium ions thereof;

wherein the second antimicrobial metal component is at least one metal selected from the group consisting of silica, silicates, silicon dioxide, borosilicates, aluminosilicates, alumina, aluminum phosphate, zinc, zinc oxide, zinc silicate, copper, copper oxide, and mixtures thereof; and treating the coated substrate to produce at least a partially hardened and adhered antimicrobial coating on the final sheet product.

12. A process of manufacturing a metal sheet precoated with an antimicrobial polymer coating, comprising:

providing a metal sheet substrate having two opposed planar surfaces comprising a base metal selected from the group consisting of aluminum, iron, nickel, titanium, molybdenum, magnesium, manganese, copper, silver, lead, tin, chromium, beryllium, tungsten, cobalt and alloys thereof;

cleaning the surface of the substrate wherein cleaning comprises deoxidizing the surface by immersion in an acid solution, and rinsing in water;

pretreating at least one planar surface of the substrate to promote adhesion of a polymer coating;

applying a polymer coating onto at least one planar surface of the substrate by roll coating the substrate with a polymer containing an anti-microbial powder comprising core particles associated with an antimicrobial metal component;

wherein the content of the antibiotic powder is in the range of from about 0.2 to about 30 weight percent of the polymeric coating;

wherein the core particle comprises one or more particles selected from the group consisting of: oxides selected from the group consisting of titanium, aluminum, zinc and copper oxides, sulfates selected from the group consisting of calcium, strontium and barium sulfates, sulfides selected from the group consisting of zinc and copper sulfides, zeolites, zirconium phosphate, mica, talc, kaolin, mullite, silica and mixtures thereof;

wherein the antimicrobial metal component is selected from the group consisting of silver, copper, zinc, mercury, tin, lead, bismuth, cadmium, chromium, cobalt, nickel, and thallium ions and mixtures thereof; and treating the coated substrate to produce at least a partially hardened and adhered antimicrobial coating on the final sheet product.

* * * * *